US010744177B2

(12) United States Patent
Arvik (10) Patent No.: US 10,744,177 B2
(45) Date of Patent: Aug. 18, 2020

(54) THERAPEUTIC USE OF GRAPE SEED PRODUCTS

(71) Applicant: Sonomaceuticals, LLC, Santa Rosa, CA (US)

(72) Inventor: Torey James Arvik, Santa Rosa, CA (US)

(73) Assignee: SONOMACEUTICALS, LLC, Santa Rosa, CA (US)

( * ) Notice: Subject to any disclaimer, the term of this patent is extended or adjusted under 35 U.S.C. 154(b) by 258 days.

(21) Appl. No.: 15/305,007

(22) PCT Filed: Apr. 21, 2015

(86) PCT No.: PCT/US2015/026825
§ 371 (c)(1),
(2) Date: Oct. 18, 2016

(87) PCT Pub. No.: WO2015/164341
PCT Pub. Date: Oct. 29, 2015

(65) Prior Publication Data
US 2017/0173102 A1    Jun. 22, 2017

Related U.S. Application Data

(60) Provisional application No. 61/982,133, filed on Apr. 21, 2014.

(51) Int. Cl.
*A61K 36/00* (2006.01)
*A61K 36/87* (2006.01)

(52) U.S. Cl.
CPC .................... *A61K 36/87* (2013.01)

(58) Field of Classification Search
CPC ........................................... A61K 36/00
USPC ........................................... 424/725
See application file for complete search history.

(56) References Cited

U.S. PATENT DOCUMENTS

| | | | |
|---|---|---|---|
| 8,492,110 | B2 | 7/2013 | Qi et al. |
| 2002/0192314 | A1 | 12/2002 | Cho et al. |
| 2006/0172012 | A1 | 8/2006 | Finely et al. |
| 2009/0082738 | A1 | 3/2009 | Vad |
| 2010/0260733 | A1 | 10/2010 | Qi |
| 2011/0217417 | A1 | 9/2011 | Perlman |

FOREIGN PATENT DOCUMENTS

| | | |
|---|---|---|
| AU | 1951200 A | 8/2001 |
| CN | 101277616 A | 10/2008 |
| DE | 202009013228 U1 | 2/2011 |
| WO | 2005048719 | 2/2005 |
| WO | 2011039308 A3 | 5/2011 |
| WO | 2013165921 A1 | 11/2013 |

OTHER PUBLICATIONS

Yun Ju Woo et al. Grape seed proanthocyanidin extract ameliorates monosodium iodoacetate-induced osteoarthritis, 2011 Exp. Mol. Med. vol. 43:10, p. 561-570.
Janisch et al., "Simulated Digestion of Vitis vinifera seed powder: Polyphenolic content and antioxidant properties", J. Agric. Food Chem. 2006, 54, p. 4839-4848.
Notice of Allowance dated Jun. 18, 2018 in U.S. Appl. No. 14/398,093.
D'Alonzo, Scope and Impact of Allergic Rhinitis, Jun. 2002, S2-6, 102(6 Suppl 2).
Hoye, Value-added Product Development Utilizing Washington State Grape Seed Flour, Doctoral Dissertation, Thesis submitted Washington State University, School of Food Science, 2009.
Shi, Optimization of the Extraction of Polyphenols From Grape Seed Meal by Aqueous Ethanol Solution, Journal of Food Agriculture & Environment, 2003, 42-47, vol. 1 (2).
Di Castelnuovo, Consumption of Cocoa, Tea and Coffee and Risk of Cardiovascular Disease, European Journal of Internal Medicine, 2012, 15-25, 23.
Hogan, Dietary Supplementation of Grape Skin Extract Improves Glycemia and Inflammation in Diet-induced Obese Mice Fed a Western High Fat Diet, J Agric Food Chern, 2011, 3035-3041, 59.
Hooper, Flavonoids, Flavonoid-rich Foods, and Cardiovascular Risk: A Meta-analysis of Randomized Controlled Trials, Am J Clin Nutr, 2008, 38-50, 88.
Jiao, Hypocholesterolemic Activity of Grape Seed Proanthocyanidin is Mediated by Enhancement of Bile Acid Excretion and Up-regulation of CYP7A1, J Nutri Biochem, 2010,1134-1139, 21.
Kay, The Future of Flavonoid Research, British Hournal of Nutrition, 2010, S91-S95, 104.
Keen, Cocoa Antioxidants and Cardiovascular Health, Am J Clin Nutr, 2005, 298S-303S, 81.
McCullough, Flavonoid Intake and Cardiovascular Disease Mortality in a Prospective Cohort of US Adults, Am J Clin Nutr, 2012, 454-64, 95.
Meyers, Influence of Dietary Quercetin on Glutathione Redox Status in Mice, J Agric Food Chem, 2008, 830-836, 56.
Nijjar, Role of Dietary Supplements in Lowering Low-density Lipoprotein Cholesterol: A Review, J Clin Lipid, 2010, 248-258, 4.
Russo, The Flavonoid Quercetin in Disease Prevention and Therapy: Facts and Fancies, Biochem Pharm, 2012, 6-15, 83.
Serrano, Tannis: Current Knowledge of Food Sources, Intake, Bioavailability and Biological Effects, Mol Nutr Food Res, 2009, S310-S329, 53.

(Continued)

Primary Examiner — Michael V Meller
(74) Attorney, Agent, or Firm — Troutman Pepper Hamilton Sanders LLP (57) ABSTRACT

The present disclosure relates to compositions and therapeutic uses of Chardonnay grape product and other grape seed products. In one embodiment, the grape seed product is used to treat or prevent joint pain or inflammation or to maintain healthy joints. The grape seed product can be the defatted portion of Chardonnay seed, such as Chardonnay pomace meal, Chardonnay pomace flour, Chardonnay seed meal, or, in some embodiments, Chardonnay seed flour or seed extract. Such products can be administered as a food or beverage.

10 Claims, 2 Drawing Sheets

(56) References Cited

OTHER PUBLICATIONS

Shanmuganayagam, Differential Effects of Grape (*Vitis vinifera*) Skin Polyphenolics on Human Platelet Aggregation and Low-density Lipoprotein Oxidation, J Agric Food Chem, 2012, 5787-5794, 60(23).

Shrime, Flavonoid-rich Cocoa Consumption Affects Multiple Cardiovascular Risk Factors in a Meta-analysis of Short-term Studies, J Nutr, 2011, 1982-1988, 141.

Soto, Antioxidant Activity and Consumer Acceptance of Grape Seed Flour-containing Food Products, International Journal of Food Science and Technology, 2012, 592-602, 47.

Vislocky, Biomedical Effects of Grape Products, Nutri Rev, 2010, 656-670, 68(1).

Weseler, Pleiotropic Benefit of Monomeric and Oligomeric Flavanols on Vascular Health—a Randomized Controlled Clinical Pilot Study, PLOS One, 2011, e28460, 6(12).

Yano, Improvements in the Bread-making Quality of Gluten-free Rice Batter by Glutathione, J Agric Food Chern, 2010, 7949-7954, 58.

Yunoki, Effect of Dietary Wine Pomace Extract and Oleanolic Acid on Plasma Lipids in Rats Fed High-fat Diet and Its DNA Microarray Analysis, J Agric Food Chem, 2008, 12052-12058, 56.

Zheng, Green Tea Intake Lowers Fasting Serum Total and LDL Cholesterol in Adults: A Meta-analysis of 14 Randomized- Randomized Controlled Trials, Am J Clin Nutr, 2011, 601-610, 94.

Decorde, Chardonnay Grape Seed Procyanidin Extract Supplementation Prevents High-fat Diet-induced Obesity in Hamsters by Improving Adipokine Imbalance and Oxidative Stress Markers, Mol Nutr Foods Res, 2009, 659-666, 53(5).

Decorde, Chardonnay Grape Seed Procyanidins Prevent Obesity in Hamsters, Agro Food Industry Hi-Tech, 2009, 24-26, 20(6).

Auger, Polyphenols-enriched Chardonnay White Wine and Sparkling Pinot Noir Red Wine Identically Prevent Early Atherosclerosis in Hamsters, J Agric Food Chem, 2005, 9823-9829, 53(25).

Tamura, Method for Preparing Fruit with Enhanced Gamma-aminobutyric Acid Having Blood Pressure Lowering, Tranquilizing, and Obesity Preventing Effects, Database TCM [Online]2008 (XP-002708065).

Fiechtner-Mors, Effects of Moderate Consumption of White Wine on Weight Loss in Overweight and Obese Subjects, Int J Obes Relat Melab Disord, 2004, 1420-1426, 28(11).

Landrault, Antioxidant Capacities and Phenolics Levels of French Wines from Different Varieties and Vintages, 2001, 3341-3348, 49(7).

Joosten, Moderate Alcohol Consumption Increases Insulin Sensitivity and ADIPOQ Expression in Postmenopausal Women: A Randomised, Crossover Trial, Diabelologia, 2008, 1375-1381, 51(8).

Landrault, Effect of a Polyphenols-enriched Chardonnay White Wine in Diabetic Rats, J Argic Food Chem, 2003, 311-318, 51.

Kokavec, Effect on Plasma Insulin and Plasma Glucose of Consuming White Wine Alone After a Meal, Alcohol Clin Exp Res, 2003, 1718-1723, 27(11).

International Search Report dated Jul. 6, 2015 for application No. PCT/US15/26825.

Written Opinion dated Jul. 6, 2015 for application No. PCT/US15/26825.

Lutterodt et al., Fatty acid composition, oxidative stability, antioxidant and antiproliferative properties of selected cold-pressed grape seed oils and flours, Food Chemistry 2011 128(2):391-399.

Thiruchenduran et al., Protective effect of grape seed proanthocyanidins against cholesterol cholic acid diet-induced hypercholesterolemia in rats, Cardiovascular Pathology 2011 20(6):361-368.

Yamakoshi et al., Effect of proanthocyanidin-rich extract from grape seeds on human fecal flora and fecal odor, Microbial Ecology in Health and Disease 2011 13:25-31.

THERAPEUTIC USE OF GRAPE SEED PRODUCTS

BACKGROUND

It is estimated that 1 out of 5 Americans suffer from allergies. Allergic rhinitis, a common allergy also known as hay fever, is estimated to affect 40 million people in the United States and was estimated to account for $7.9 billion dollars of direct and indirect costs in 1997. J Am Osteopath Assoc. 2002 June; 102(6 Suppl 2):S2-6.

Allergic reactions occur when the immune system reacts to a normally harmless environmental substance. For example, hay fever is often caused by exposure to pollen, dust mites, or pet dander. Symptoms of hay fever include runny nose, watery or itchy eyes, sneezing, and coughing. Treatment of hay fever and other allergies includes avoidance of the allergen that causes the allergic reaction, over-the-counter medications such as antihistamines, and prescription medications such as steroid nasal sprays.

Thus, there is a need to identify agents that can treat or prevent allergic reactions such as hay fever. Embodiments disclosed herein fulfill these needs as well as others.

Vitamin D plays a role in intestinal absorption of calcium and phosphate, and vitamin D deficiency has been associated with rickets in children and osteoporosis in adults. Vitamin D deficiency can result from inadequate sun exposure coupled with inadequate nutritional intake or absorption of vitamin D.

Thus, there is a need to identify agents that can improve absorption of vitamin D derived from dietary sources. Embodiments disclosed herein fulfill these needs as well as others.

Joint pain can be caused by many different conditions such as osteoarthritis, rheumatoid arthritis, bursitis, gout, strains, sprains, and other injuries. Joint pain is often accompanied by inflammation. Over-the-counter or prescription non-steroidal anti-inflammatory drugs (NSAIDs) such as aspirin, ibuprofen, naproxen, and celecoxib are often used to treat moderate to severe joint pain and inflammation. However, NSAIDs can have undesirable side effects such as gastrointestinal bleeding.

Thus, there is a need to identify agents that can treat or prevent joint pain and inflammation. Embodiments disclosed herein fulfill these needs as well as others.

SUMMARY

The present disclosure relates to a method of treating or preventing an allergic reaction in a subject by administering an amount of Chardonnay seed product, other grape seed product, or a combination thereof that is effective to treat or prevent the allergic reaction.

In some embodiments, the allergic reaction is hay fever or characterized as hay fever.

In some embodiments, the allergic reaction is caused by exposure to one or more environmental airborne allergens. In some embodiments, the one or more airborne allergens are selected from plant pollens, e.g., tree, grass, or ragweed pollen, dust mites, dust mite feces, mold, animal dander, animal fur, and combinations of any of the foregoing.

In some embodiments, administration of the Chardonnay seed product, other grape seed product, or a combination thereof is effective to reduce symptoms associated with an allergic reaction such as red eyes, itchy eyes, watery eyes, runny nose, bronchoconstriction, and/or sneezing.

The present disclosure further relates to a method of treating or preventing a vitamin D deficiency by administering an amount of Chardonnay seed product, other grape seed product, or a combination thereof that is effective to treat or prevent a vitamin D deficiency. In some embodiments, the method further comprises administration of a vitamin D supplement.

Embodiments disclosed herein provide methods of treating, alleviating, or preventing pain and/or inflammation by administering an amount of Chardonnay seed product, other grape seed product, or a combination thereof that is effective to treat, alleviate or prevent pain and/or inflammation. In some embodiments, the pain is joint pain. In some embodiments, the inflammation is arthritis. In some embodiments, the inflammation is joint inflammation. In some embodiments, the joint is a synovial joint. In some embodiments, the joint pain is in the knee, wrist, shoulder, elbow, ankle, hip, or fingers. Accordingly, in some embodiments, the method comprises administering a Chardonnay seed product, other grape seed product, or a combination thereof to treat or alleviate synovial joint pain.

In some embodiments of the methods, a second grape seed or grape skin product which is not a Chardonnay seed product is administered to the mammal. In certain embodiments, the combination of Chardonnay seed product and second grape seed or grape skin product provides a therapeutic effect or health benefit which is greater than the effect of administration of Chardonnay seed product alone. In some embodiments, the second grape seed or skin product is administered simultaneously with the first grape seed or first grape skin product. The two different grape seed or skin products can be administered in the same composition or different compositions.

In some embodiments, the grape seed product is prepared from seeds having an epicatechin content of at least 600 mg of epicatechin per 100 g of seeds or an epicatechin content of at least 700 mg of epicatechin per 100 g of seeds. In some embodiments, the epicatechin content ranges from 600-800 mg/100 g of seeds or from 650-800 mg/100 g of seeds. In some embodiments, the epicatechin content ranges from 100-900 mg/100 g of seeds or as otherwise described herein.

In some embodiments, the grape seed product is incorporated into a food or beverage product.

In some embodiments, the Chardonnay seed product is Chardonnay seed flour. In certain embodiments, the Chardonnay seed product is Chardonnay seed extract. In certain embodiments, the Chardonnay seed product is from grapes grown in a Winkler region climate type I, II, III, IV, or V.

In some embodiments, methods of supporting or maintaining healthy joints in a subject are provided. In some embodiments, the methods comprise administering to a subject a Chardonnay seed product, other grape seed product, or a combination thereof in an amount effective to support or maintain healthy joints.

In some embodiments, methods of supporting or maintaining healthy joint range of motion, joint mobility, and/or joint strength in a subject are provided. In some embodiments, the methods comprise administering to a subject a Chardonnay seed product, other grape seed product, or a combination thereof in an amount effective to support or maintain healthy joint range of motion, joint mobility, and/or joint strength in the subject.

In some embodiments, methods of improving joint range of motion, increasing joint mobility, and/or increasing joint strength in a subject are provided. In some embodiments, the methods comprise administering to a subject a Chardonnay seed product, other grape seed product, or a combination thereof in an amount effective to improve joint range of motion, increase joint mobility, and/or increase joint strength

DETAILED DESCRIPTION

As used herein, the terms "a" or "an" means that "at least one" or "one or more" unless the context clearly indicates otherwise.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps. Although various methods and compositions may refer to comprising language, it is evident that they also include methods and compositions consisting of or consisting essentially of the elements recited herein.

As used herein, the phrase "effective amount" or equivalents thereof means the amount of compound or composition that elicits the response that is being sought, such as but not limited to, treating or alleviating pain, supporting or maintaining healthy joints as well as the other uses described herein in a subject. The effect is dependent upon method or the effect desired. As such, the effect can be a decrease in the severity of symptoms associated with the condition and/or inhibition (partial or complete) of progression of the condition, or improved treatment, healing, prevention or elimination of a disorder, or side-effects. The amount needed to elicit the response can be determined based on the age, health, size and sex of the subject. Optimal amounts can also be determined based on monitoring of the subject's response to treatment. Non-limiting examples of "effective amounts" are provided herein.

The present embodiments relate to Chardonnay and other grape seed products and methods of treating or preventing an allergic reaction, e.g., hay fever, and other conditions, e.g., vitamin D deficiency, pain, or inflammation using Chardonnay and other grape seed products. In some embodiments, the Chardonnay seed products are produced from grapes grown in Winkler region climate types I-IV (Jones et al., 2010, Am. J. Enol. Vitic. 61(3):313-326). In some embodiments, the Chardonnay seed products are produced from grapes grown in the coastal valleys of Northern California, e.g., the Napa Valley and/or the Sonoma Valley. In another embodiment, the Chardonnay seed products are produced from grapes grown in other, hotter, inland valley vineyards, e.g., in Winkler region climate types IV-V. In some embodiments, the Chardonnay seed product is from grapes grown in a coastal region.

In some embodiments, the Chardonnay seed products contain the defatted portion of Chardonnay seed, such as Chardonnay pomace meal, Chardonnay pomace flour, Chardonnay seed meal, or, in some embodiments, Chardonnay seed flour. In some embodiments, the Chardonnay seed product includes the contents of defatted Chardonnay seeds that are not extractable by an organic solvent, e.g., are not extractable by ethanol and/or methanol. In some embodiments, the Chardonnay seed product is prepared from seeds having an epicatechin content of at least 600 mg of epicatechin per 100 g of seeds or an epicatechin content of at least 700 mg of epicatechin per 100 g of seeds. In some embodiments, the Chardonnay seed product is prepared from seeds having an epicatechin content of at least, or about, 100, 200, 300, 400, 500, 600, 700, 800, or 900 mg of epicatechin per 100 g of seeds. In some embodiments, the epicatechin content is about 600-800 mg/100 g of seeds or about 650-800 mg/100 g of seeds. In some embodiments, the epicatechin content is about 100-900 mg/100 g of seeds, about 100-800 mg/100 g of seeds, about 100-700 mg/100 g of seeds, about 100-600 mg/100 g of seeds, about 100-500 mg/100 g of seeds, about 100-400 mg/100 g of seeds, about 100-300 mg/100 g of seeds, about 100-200 mg/100 g of seeds, about 200-900 mg/100 g of seeds, about 200-800 mg/100 g of seeds, about 200-700 mg/100 g of seeds, about 200-600 mg/100 g of seeds, about 200-500 mg/100 g of seeds, about 200-400 mg/100 g of seeds, about 200-300 mg/100 g of seeds, about 300-900 mg/100 g of seeds, about 300-800 mg/100 g of seeds, about 300-700 mg/100 g of seeds, about 300-600 mg/100 g of seeds, about 300-500 mg/100 g of seeds, about 300-400 mg/100 g of seeds, about 400-900 mg/100 g of seeds, about 400-800 mg/100 g of seeds, about 400-700 mg/100 g of seeds, about 400-600 mg/100 g of seeds, about 400-500 mg/100 g of seeds, about 500-900 mg/100 g of seeds, about 500-800 mg/100 g of seeds, about 500-700 mg/100 g of seeds, about 500-600 mg/100 g of seeds, about 600-900 mg/100 g of seeds, about 600-800 mg/100 g of seeds, about 600-700 mg/100 g of seeds, about 700-900 mg/100 g of seeds, about 700-800 mg/100 g of seeds, or about 800-900 mg/100 g of seeds.

As used herein, "Chardonnay seed meal" is ground whole seeds and "Chardonnay seed flour" is ground seed after the oil has been extracted. Chardonnay seed flour may be obtained using the "cold press", "hot press" and solvent extraction processes as are known in the art to extract the oil from seeds yielding defatted seed flour. The meal or flour can be dried to the desired moisture content using conventional drying techniques suitable for drying food products.

The dried meal or flour is further ground under ambient temperature conditions to form Chardonnay seed powder having free-flowing particles. In some embodiments, the free-flowing particles can range from a size not exceeding 841 microns (20 mesh) to a size not exceeding 37 microns (400 mesh). In certain embodiments, the size does not exceed 20 mesh, 40 mesh, 60 mesh, 80 mesh, 100 mesh, 200 mesh, 300 mesh, or 400 mesh.

In an exemplary method, Chardonnay seed flour is made by separating and drying Chardonnay grape seeds, for example from the pomace produced after Chardonnay grapes are pressed to produce grape juice (e.g., to make wine). The grape seeds can be "cold-pressed" to defat them (producing Chardonnay seed oil as a byproduct). Grape seed flours are milled from the press cake after the oil is expelled. In one embodiment, after juicing the grape the seed is separated from the skins, cleaned, mechanically defatted, finely milled and sifted to create an 100 mesh (150 micron) flowable powder.

Chardonnay seed flour can also be purchased from Apres Vin (Yakima, Wash.), Botanical Oil Innovations (Spooner, Wis.) or Fruitsmart, Inc. (Grandview, Wash.). The FruitSmart Chardonnay seed flour is an 85 mesh flowable powder but can be further milled and sifted to produce a flour with a smaller particle size.

In some embodiments, skins, stems and leaves (the remainder of pomace) are removed from the seeds prior to pressing. Removal of the skins, stems, and leaves allows for optimal oil pressing.

"Chardonnay seed extract" is made by solvent extraction of Chardonnay seeds with a suitable solvent, such as ethanol or methanol. For example, "40EtChrSdEx" is a Chardonnay seed extract made using a 40% ethanol solution as the extraction solvent. The extraction process, in addition to the extract containing the solvent soluble components, also produces a residue of non-soluble solids.

In addition to the Chardonnay seed products disclosed herein other grape seed products can also be used in the methods. The other grape seed products can be used in the place of, or in combination with, the Chardonnay seed products. Examples of other grape seed products include, but are not limited to, Syrah grape seed products, Cabernet Sauvignon grape seed products, Pinot Noir grape seed products, Sauvignon Blanc grape seed products, White Riesling grape seed products, and the like. In some embodiments, the grape seed product is a Winkler V grape. The product can be a flour or an extract of the grape seed.

In some embodiment of the methods and uses disclosed herein, the amount of grape seed product or extract (e.g. Chardonnay seed flour or extract) consumed as a percentage of daily diet is at least, or about, 3%, at least, or about, 5%, or at least, or about, 8% by mass. In some embodiments, the amount is about 1-10%, about 5-10%, about 7%, or about 10% of the daily diet by mass.

In some embodiments, the amount consumed or administered is a therapeutically effective amount for a use or method described herein or an amount sufficient to maintain or support healthy joints, joint range of motion, joint mobility, and joint strength.

In some embodiments of the methods, the amount of Chardonnay seed flour consumed or administered as a percentage of daily diet is at least, or about, 3%, at least, or about, 5%, or at least, or about, 8% of total calories consumed. In some embodiments, about 1-10%, 5-10%, 7%, or 10% of the daily calories are from Chardonnay seed flour.

In some embodiments, the amount of Chardonnay seed flour consumed daily is at least, or about, 10 g, at least, or about, 15 g, at least, or about, 20 g, at least, or about, 25 g, at least, or about, 30 g, at least, or about, 35 g, at least, or about, 40 g, or at least, or about, 45 g. In some embodiments, at least, or about, 50 g of Chardonnay seed flour is consumed daily. In some embodiments, the amount is at least, or about, 50 mg, 100 mg, 200 mg, 300 mg, 400 mg, 500 mg, 600 mg, 700 mg, 800 mg, 900 mg, or 1000 mg. In some embodiments, the amount is at least, or about, 100 to 1000 mg, 200 to 1000 mg, 300 to 1000 mg, 400 to 1000 mg, 500 to 1000 mg, 600 to 1000 mg, 700 to 1000 mg, 800 to 1000 mg, or 900 to 1000 mg.

In some embodiments, the amount of Chardonnay seed flour consumed daily is at least 1 tablespoon, at least 2 tablespoons, at least 3 tablespoons, at least 4 tablespoons, or at least 5 tablespoons.

In another embodiment, the amount of Chardonnay seed flour consumed daily on a Chardonnay seed flour weight: body weight basis is at least 0.2 g/kg, at least 0.5 g/kg, or at least 0.7 g/kg. In some embodiments, at least 1 g of Chardonnay seed flour per kg of body weight is consumed per day.

The amounts consumed or administered can be taken once a day, twice a day, three times a day, or four times a day. In some embodiments, the amount is consumed or administered every 2, 4, 6, 8, 12, 18 or 24 hours.

Chardonnay seed flour can be substituted with Chardonnay pomace meal, pomace flour, skin flour, seed extract, or seed meal in any of the methods or embodiments disclosed herein. The amount of Chardonnay pomace meal, pomace flour, skin flour, seed extract, or seed meal that will need to be consumed daily to attain the same benefit as a given amount of Chardonnay seed flour can readily be determined by those skilled in the art. For example, it is expected that a subject will need to consume about three times as much Chardonnay skin flour to achieve the same benefit as a given amount of Chardonnay seed flour.

In some embodiments, the Chardonnay seed product, e.g., Chardonnay seed flour, is taken at least twice a week, at least 3 times a week, or every other day. In some embodiments, the Chardonnay seed product is incorporated into the daily diet.

The Chardonnay seed product, e.g., Chardonnay seed flour, can be taken for an amount of time sufficient to treat and/or prevent a condition amenable to treatment and/or prevention by Chardonnay seed product as described herein. The Chardonnay seed product a can be taken for at least one week, at least 2 weeks, at least 3 weeks, at least one month, at least 2 months, at least 3 months, at least 6 months, at least a year, or indefinitely.

In some embodiments of the methods, a second grape seed or grape skin product which is not a Chardonnay seed product is administered to the mammal. In some embodiments, the combination of Chardonnay seed product and second grape seed or grape skin product provides a therapeutic effect or health benefit which is greater than the effect of administration of Chardonnay seed product alone.

In other embodiments, the amount of Chardonnay seed product and amount of the second grape seed or grape skin product are selected so that the effect achieved is at least the same as the effect achieved by a given amount of Chardonnay seed product administered alone.

The Chardonnay seed products can be included in a variety of food products, such as nutritional beverages (e.g., nutritional shakes), baked goods (e.g., cookies, brownies, cake, breads, biscuits, crackers), puddings, confections (i.e., candy), snack foods (e.g., pretzels), ice cream, frozen confections and novelties, or non-baked, extruded food products such as bars, including health or energy bars. The Chardonnay seed product can also be provided as a nutritional supplement, either in tablet form or as a powder for use as a nutritional food additive.

In one embodiment, the Chardonnay seed product can be blended with other dry food materials for use in the preparation of food products enriched with Chardonnay seed products. Dry food materials include, for example, dry starch-containing materials, dry protein-containing materials or combinations thereof. Suitable starch-containing materials may be derived from, for example, rice, corn, soybeans, sunflower, canola, wheat, oats, rye, potato, or any combination thereof. Suitable dry protein-containing materials may be derived from for example, meat, milk, fish or any combination thereof. For baking applications, the Chardonnay seed product is suitable used in an amount ranging from 3% to 15% of the dry food material (e.g., white or whole wheat flour). In some embodiments, the amount used is about 0.5% to about 15%, 0.5% to about 14%, about 0.5% to about 13%, about 0.5% to about 12%, about 0.5% to about 11%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, about 0.5% to about 1%, about 1% to about 15%, 1% to about 14%, about 1% to about 13%, about 1% to about 12%, about 1% to about 11%, about 1% to about 10%, about 1% to about 9%, about 1% to about 8%, about 1% to about 7%, about 1% to about 6%, about 1% to about 5%, about 1% to about 4%, about 1% to about 3%, about 1% to about 2%, about 2% to about 15%, 2% to about 14%, about 2% to about 13%, about 2% to about 12%, about 2% to about 12%, about 2% to about 10%, about 2% to about 9%, about 2% to about 8%, about 2% to about 7%, about 2% to about 6%, about 2% to about 5%, about 2% to about 4%, about 2% to about 3%, about 3% to about 15%, 3% to about 14%, about 3% to about 13%, about 3% to about 13%, about 3% to about 13%, about 3% to about 10%, about 3% to about 9%, about 3% to about 8%, about 3% to about 7%, about 3% to about 6%, about 3% to about 5%, about 3% to about 4%, about 4% to about 15%, 4% to about 14%, about 4% to about 14%, about 4% to about 14%, about 4% to about 14%, about 4% to about 10%, about 4% to about 9%, about 4% to about 8%, about 4% to about 7%, about 4% to about 6%, about 4% to about 5%, about 5% to about 15%, 5% to about 15%, about 5% to about 15%, about 5% to about 15%, about 5% to about 15%, about 5% to about 10%, about 5% to about 9%, about 5% to about 8%, about 5% to about 7%, about 5% to about 6%, about 6% to about 16%, 6% to about 16%, about 6% to about 16%, about 6% to about 16%, about 6% to about 16%, about 6% to about 10%, about 6% to about 9%, about 6% to about 8%, about 6% to about 7%, The dry food may optionally also include additional ingredients such as vitamins, mineral fortifiers, salts, colors, flavors, flavor enhancers or sweeteners.

Chardonnay seed products can be incorporated into beverages, processed meats, frozen desserts, confectionery products, dairy-type products, sauce compositions, and cereal grain products. Beverage products include, for example, smoothies, infant formula, fruit juice beverages, yogurt beverages, coffee beverages, beer, dry beverage mixes, tea fusion beverages, sports beverages, soy liquors, soda, slushes, and frozen beverage mixes. Meat products include, for example, ground chicken products, water-added ham products, bologna, hot dogs, franks, chicken patties, chicken nuggets, beef patties, fish patties, surimi, bacon, luncheon meat, sandwich fillings, deli meats, meat snacks, meatballs, jerky, fajitas, bacon bits, injected meats, and bratwurst. Confectionery products include, for example, chocolates, mousses, chocolate coatings, yogurt coatings, cocoa, frostings, candies, energy bars, and candy bars. Frozen dessert products include, for example, ice cream, malts, shakes, popsicles, sorbets, and frozen pudding products. Dairy-type products include, for example, yogurt, cheese, ice cream, whipped topping, coffee creamer, cream cheese, sour cream, cottage cheese, butter, mayonnaise, milk-based sauces, milk-based salad dressings, and cheese curds. Cereal grain products include, for example, breads, muffins, bagels, pastries, noodles, cookies, pancakes, waffles, biscuits, semolina, chips, tortillas, cakes, crackers, breakfast cereals (including both ready-to-eat and cooked cereals), pretzels, dry bakery mixes, melba toast, breadsticks, croutons, stuffing, energy bars, doughnuts, cakes, popcorn, taco shells, fry coatings, batters, breading, crusts, brownies, pies, puffed soy cakes, crepes, croissants, flour, and polenta. Sauce compositions include salad dressings, nut butter spreads (e.g., peanut butter spreads), marinades, sauces, salsas, jams, cheese sauces, mayonnaise, tartar sauce, soy humus, dips, fruit syrups, and maple syrups. Sauce composition may also include a suspending agent to aid in maintaining the uniformity of the composition. Examples of suitable suspending agents include polysaccharides, such as starch, cellulose (e.g., microcrystalline cellulose) and carrageenan, and polyuronides, such as pectin. Gelatin is another example of a suspending agent which may be used in the beverage compositions as well. Examples of additional supplemented food products prepared using the premixes described herein include, but are not limited to, tofu, formulated soy essence, powdered protein supplements, juice mixable protein supplements, foaming agents, clouding agents, baby foods, meatless balls, meat analogues, egg products (e.g., scrambled eggs), soups, chowders, broth, milk alternatives, soy-milk products, chili, spice mixes, sprinkles, soy whiz, salad topping, edible films, edible sticks, chewing gum, bacon bits, veggie bits, pizza crust barriers, soy pie, no-gas synthetic beans, soy helper, soy cotton candy, fruit bits, pizza rolls, mashed potatoes, spun soy protein fiber, soy roll-ups, extruded snacks, condiments, lotions, fries, gelatin dessert products, vitamin supplements, nutritional bars, dry cake, bread or muffin mixes, and microwavable instant dry mixes.

In some embodiments, the Chardonnay seed product may be provided as an energy bar (suitable for consumption during physical activity) or a meal replacement bar. The energy bar or meal replacement bar can also contain one or more vitamin, mineral, food supplement, botanical, or plant or herb extracts or ingredients known in the art or used in energy bars or meal replacement bars, such as a fruit juice or extract, an herb or herb flavor, natural or artificial flavors, vitamins, minerals, anti-oxidant containing extracts, coenzyme Q, omega-3 fatty acids, guarana, caffeine, theobromine, maltodextrin, and protein. In some embodiments, the energy bar or meal replacement bar can have total available energy levels of carbohydrates/protein/fat of 40/30/30 respectively.

The energy and meal replacement bars can be further supplemented for athletic performance enhancement, mental energy or cognitive focus enhancement, and/or nutritional benefit. Exemplary supplements include, but are not limited to Vinpocetine, Vincamine *Ginkgo Biloba*, L-Arginine, Acetyl-L-Carnitine, Feverfew, DMAE (Dimethylaminoethanol), DMAE bitartrate, P-chlorophenoxyacetate, Vitamin B-Complex, *Ginseng*, 5 HTP (5-Hydroxytryptophan), L-Theanine, Androstenedione, L-Glutamine, L-Tyrosine, L-Glycine; L-lysine; Whey Protein; DHEA (Dehydroepiandrosterone).

The Chardonnay seed composition can also contain an amount of a second grape seed or grape skin product which is not a Chardonnay seed product. In some embodiments, an amount of Chardonnay seed product is replaced in the Chardonnay seed composition with an amount of the second grape seed or grape skin product. The amount of second grape seed or grape skin product that will need to be added to the Chardonnay seed composition to attain the same benefit as a given amount of Chardonnay seed product can readily be determined by those skilled in the art.

In some embodiments, a composition comprising a Chardonnay seed flour composition, is administered to a subject, such as, but not limited to, a mammal (e.g. a human subject) in which treatment or prevention of an allergic reaction is useful desired.

In some embodiments, a composition comprising a Chardonnay seed flour composition, is administered to a subject, such as, but not limited a mammal (e.g. a human subject), in which treatment or prevention of a vitamin D deficiency is useful or desired.

In some embodiments, a composition comprising a Chardonnay seed flour composition, is administered to a subject, such as, but not limited a mammal (e.g. a human subject), in which treatment or prevention of pain and/or inflammation is useful or desired.

As used herein, "treatment" or "treating" refers to an amelioration of a disease or disorder, or at least one discernible symptom thereof "Treatment" or "treating" can also refer to an amelioration of at least one measurable physical parameter, not necessarily discernible by the subject. "treatment" or "treating" can also refer to inhibiting the progression of a disease or disorder, either physically, e.g., stabilization of a discernible symptom, physiologically, e.g., stabilization of a physical parameter, or both.

In some embodiments, the compositions described herein are administered to a subject, (e.g. a mammal, which include, but is not limited to, a human), as a preventative measure against a disease or disorder. As used herein, "prevention" or "preventing" refers to a reduction of the risk of acquiring a given disease or disorder. In some embodiments, the compositions are administered as a preventative measure to a subject, such as, but not limited to, a human having a predisposition, e.g., a genetic predisposition to allergies, vitamin D deficiency, pain (e.g. joint pain), or inflammation. In some embodiments, the compositions are administered or consumed to treat (alleviate) joint pain. In some embodiments, the compositions are administered or consumed to improved range of motion, increased mobility, and enhance strength. In some embodiments, the compositions are consumed or administered to support or maintain healthy joints, range of motion, increased mobility, and strength.

In some embodiments, the compositions are administered as a preventative measure to a subject having a non-genetic predisposition to allergies, vitamin D deficiency, pain, or inflammation.

In some embodiments, the mammal consumes a high-fat diet. In some embodiments, a high-fat diet is a diet in which at least 30%, 35%, or 40% of total daily calories are obtained from fat.

In some embodiments, the composition comprises a grape seed product from two different grapes or varietals. In some embodiments, a composition comprising two grape seed products can produce a synergistic result.

Embodiments disclosed herein provide methods for the treatment or prevention of an allergic reaction comprising administering to a subject a therapeutically effective amount of a Chardonnay seed flour composition.

In some embodiments, compositions are administered to a subject to treat or prevent one or more symptoms of an allergic reaction, the one or more symptoms selected from red eyes, itchy eyes, watery eyes, itchy skin, runny nose, eczema, hives, bronchoconstriction, increased production of mucus in the lungs, shortness of breath, coughing, sneezing, wheezing, abdominal pain, bloating, vomiting, diarrhea, swelling of the skin, anaphylaxis, edema, hypotension, and skin rash.

In certain embodiments, the allergic reaction is caused by exposure to one or more airborne allergens, a plant, a plant protein, e.g., latex, a food, a drug, an insect sting, or an insect bite. In certain embodiments, the airborne allergens are of plant, animal, or fungal origin. Exemplary airborne allergens of plant origin include plant pollens, e.g., tree, grass, and/or ragweed pollens. Exemplary airborne allergens of animal origin include animal dander and/or animal fur from, for example, a domestic pet (e.g. dog, cat, or rabbit), dust mites, and dust mite feces. Exemplary airborne allergens of fungal origin include spores of *Alternaria, Cladosporium, Aspergillus, Penicillium, Helmin thosporium, Epicoccum, Fusarium, Mucor, Rhizopus* and *Aureobasidium.*

In certain embodiments, the allergic reaction is allergic rhinitis, or hay fever. In other embodiments, the allergic reaction is caused by dust mites.

Embodiments disclosed herein provide methods for the treatment or prevention of a vitamin D deficiency comprising administering to a subject a therapeutically effective amount of a Chardonnay seed flour composition. The normal range of vitamin D as measured by a 25-hydroxyvitamin D blood test is 30.0 to 74.0 nanograms per milliliter (ng/mL). In some embodiments, the subject has vitamin D levels below this amount, e.g., below 30, 28, 25, 20, or 15 ng/mL. In some embodiments, the subject has vitamin D levels from 15-25 ng/mL, from 10-28 ng/mL, or from 10-20 ng/mL.

In certain embodiments, the subject consumes adequate dietary vitamin D but is unable to absorb sufficient amounts of vitamin D to prevent a vitamin D deficiency. In certain embodiments, the subject has or is susceptible to a vitamin D deficiency because the subject's gut biome fails to make vitamin D bioavailable from dietary sources, e.g., from green leafy vegetables. Chardonnay seed flour administration may remedy this problem by promoting the growth of gut bacteria that are capable of making dietary vitamin D bioavailable.

In some embodiments of the methods, Chardonnay seed flour is consumed in conjunction with a dietary vitamin D supplement in order to provide a vitamin D level that is higher than the vitamin D level obtained by dietary vitamin D supplementation alone.

Embodiments disclosed herein provide methods for the treatment or prevention of pain and/or inflammation comprising administering to a subject a therapeutically effective amount of a Chardonnay seed flour composition. In certain embodiments, the pain is joint pain caused by arthritis or a joint injury. In certain embodiments, the inflammation is caused by arthritis or joint injury.

Embodiments disclosed herein also provide for the support or maintenance of healthy joints. In some embodiments, methods for supporting or maintaining healthy joints are provided. In some embodiments, the methods comprises administering to a subject a Chardonnay seed product or other grape seed product in an amount effective to support or maintain healthy joints. In some embodiments, the method comprises administering at least one food or beverage product containing said Chardonnay seed product. In some embodiments, the Chardonnay seed product is Chardonnay seed flour. In some embodiments, the Chardonnay seed product is Chardonnay seed extract. The see product, flour, or extract can be any product described herein. In some embodiments, the seed extract is a methanol or ethanol extract. The extract can be from Chardonnay or other grape seed. The grape seed products, such as those described herein, can also be used to improve joint range of motion, increase joint mobility, and/or enhanced or increase joint strength. The grape seed products, such as those described herein, can also be used to maintain or support healthy joint range of motion, joint mobility, and/or joint strength.

In some embodiments, the seed product is administered in a seed flour equivalent amount of at least, or about, 3%, at least, or about, 5%, at least, or about, 8%, or at least, or about, 10% of the daily diet by mass. As described herein, as for each of the methods or uses described herein, the seed flour can be a Chardonnay seed flour or other grape seed flour. In some embodiments, the grape seed produce is administered in a grape seed flour equivalent amount which is 0.2 g/kg of body weight, at least 0.5 g/kg of body weight, at least 0.7 g/kg of body weight, or at least 1 g/kg of body weight per day. In some embodiments, the grape seed product is administered in an amount which is at least 10 g, at least 15 g, at least 20 g, at least 25 g, at least 30 g, at least 35 g, at least 40 g, at least 45 g, or at least 50 g per day. In some embodiments, the amount is at least, or about, 50 mg, 100 mg, 200 mg, 300 mg, 400 mg, 500 mg, 600 mg, 700 mg, 800 mg, 900 mg, or 1000 mg. In some embodiments, the amount is at least, or about, 100 to 1000 mg, 200 to 1000 mg, 300 to 1000 mg, 400 to 1000 mg, 500 to 1000 mg, 600 to 1000 mg, 700 to 1000 mg, 800 to 1000 mg, or 900 to 1000 mg. Other amounts described herein can also be used.

In some embodiments, the grape seed products described herein can be administered for the methods and uses described herein twice a week, at least 3 times a week, every other day, or daily. In some embodiments, the grape seed product is administered two, three, or four times a day.

The subjects of the methods described herein can be human. In some embodiments, the subject can be a cat or a horse or other domesticated animal that can suffer from joint pain or could benefit from maintaining or supporting healthy joints.

In some embodiments, the subject is a subject in need thereof. As used herein, the phrase "in need thereof" means that the subject has been identified or suspected as having a need for the particular method or treatment. In some embodiments, the identification can be by any means of diagnosis. In any of the methods and treatments described herein, the subject can be in need thereof. In some embodiments, the subject is in an environment or will be traveling to an environment in which a particular disease, disorder, or condition (e.g. presence of allergens) is prevalent.

In some embodiments, a composition comprising Chardonnay seed extract composition, is administered to a subject, such as, but not limited to, a human subject, for each of the uses or methods described herein. Chardonnay seed extract has similar biological effects as Chardonnay seed flour (data not shown). Without wishing to be bound by any particular theory, in some embodiments, in order to achieve a benefit which in comparable to the benefit obtained by using an amount of Chardonnay seed flour, the amount of Chardonnay seed extract administered should be an amount which provides 2-5 times the catechin levels of the amount of Chardonnay seed flour. Specific amounts of Chardonnay seed extract that will need to be consumed daily to attain the same benefit as a given amount of Chardonnay seed flour can readily be determined by those skilled in the art.

Accordingly, based upon the disclosure presented herein, methods of treating or preventing an allergic reaction, comprising administering to a subject suffering from or susceptible to allergic reactions a Chardonnay seed product or other grape seed product in an amount effective to treat or prevent the allergic reaction is provided. In some embodiments, the subject is suffering from or susceptible to hay fever. In some embodiments, the allergic reaction is red eyes, itchy eyes, watery eyes, runny nose, bronchoconstriction, and/or sneezing. In some embodiments, the Chardonnay seed product is administered in amount effective to reduce red eyes, itchy eyes, watery eyes, runny nose, bronchoconstriction, and/or sneezing. In some embodiments, the subject is or has been exposed to airborne allergens. Examples of airborne allergens can be, but not limited to, of plant, animal, or fungal origin. In some embodiments, the allergen is plant pollen. In some embodiments, the plant pollen is grass pollen. In some embodiments, the allergen is dust mites, dust mite feces, or a combination thereof. In some embodiments, the allergen is animal dander, animal fur, or a combination thereof.

Also as disclosed herein, methods treating or preventing a vitamin D deficiency are provided. In some embodiments, the method comprise administering to a subject suffering from or susceptible to a vitamin D deficiency a Chardonnay seed product or other grape seed product in an amount effective to treat or prevent the vitamin D deficiency. In some embodiments, methods of supporting or maintaining Vitamin D levels in a subject are provided. In some embodiments, the method comprise administering to a subject a Chardonnay seed product or other grape seed product in an amount effective to support or maintain Vitamin D levels in the subject. In some embodiments, the subject has a vitamin D level below 28 ng/ml, below 25 ng/ml, below 20 ng/ml, or below 15 ng/ml as measured by a 25-hydroxy vitamin D blood test.

EXAMPLE 1

Chardonnay SEED Flour to Treat Hay Fever

The subject was an adult female 50+ years old who had in the past used Claritin®, Allegra®, saline nasal sprays, and steroid nasal sprays to control severe symptoms (i.e., massive sneezing fits and congestion) of hay fever that would begin every spring.

For three consecutive spring seasons, a daily smoothie containing one tablespoon (approximately 9.5 g) of Chardonnay grape seed flour was consumed by the subject. The subject reported that after she began consuming the daily smoothie, she no longer experienced sneezing and was able to hike outside. The subject reported very minor congestion, but reported that the congestion was not severe enough to prompt the subject to take any allergy medication.

EXAMPLE 2

Chardonnay SEED Flour to Treat Hay Fever and Dust Mite Allergies, Joint Pain and Joint Inflammation The subject was an adult male 40+ years old who had in the past used Claritin® and pseudoephedrine to control symptoms of hay fever and an allergy to dust mites. The subject had also experienced general pain and inflammation in his left knee since a skiing accident in 2003.

A daily smoothie containing three tablespoons (approximately 28.5 g) of Chardonnay seed flour was consumed by the subject during allergy season. After a week of consuming the daily smoothie, a dramatic increase in lung capacity and a reduction in allergy symptoms were observed by the subject. The subject reported that he did not have to take Claritin® or pseudoephedrine to control allergy symptoms even during the height of the spring and summer allergy season in an area with a high amount of agricultural activity.

After a few weeks of consuming the daily smoothie containing three tablespoons of Chardonnay seed flour, the subject observed that he had no longer experienced knee pain and knee inflammation.

EXAMPLE 3

Chardonnay See Flour to Treat Hay Fever and Vitamin d Deficiency

The subject was an adult male 60+ years old who had suffered from severe allergies for most of his life. As a child, he could not breathe through his nose during parts of the year due to hay fever. He had used pseudoephedrine and other, newer allergy medications in recent years to treat the symptoms of hay fever. The subject had in the past experienced symptoms of asthma and food allergies (i.e., wheezing) which he would treat with Benadryl®. In addition, the subject had historically low blood levels of vitamin D and was taking a dietary vitamin D supplement (3000 IBU/day) at the direction of a physician in order to achieve normal blood levels of vitamin D.

The subject started consuming a diet comprising 7-10% (w/w) dietary Chardonnay seed four. After he began consuming Chardonnay seed flour, the subject observed that his sinuses were clear all the time, including upon waking. In the year since he began consuming Chardonnay seed flour, the subject has only taken allergy medication once or twice and it was only taken to help the subject sleep. Since he began consuming Chardonnay seed flour, the subject has not needed to take any Benadryl® to treat a food allergy. Finally, the subject reported that he takes more Chardonnay seed flour when he senses an allergic reaction and that he feels better after taking the additional Chardonnay seed flour.

Figure 1:
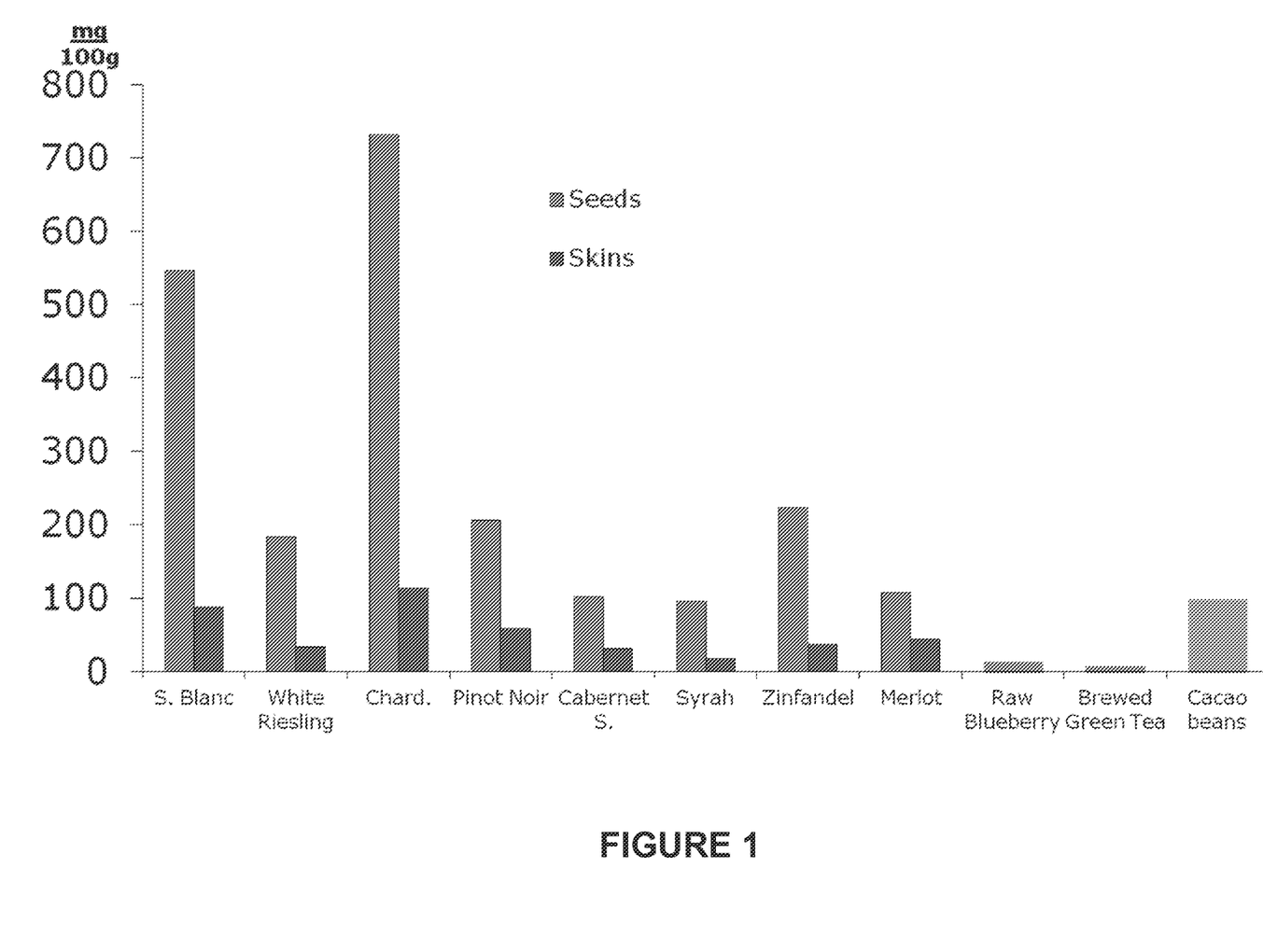
FIG. 1. Illustrates epicatechin levels in the seed and skin of different grape varieties.
Figure 2:
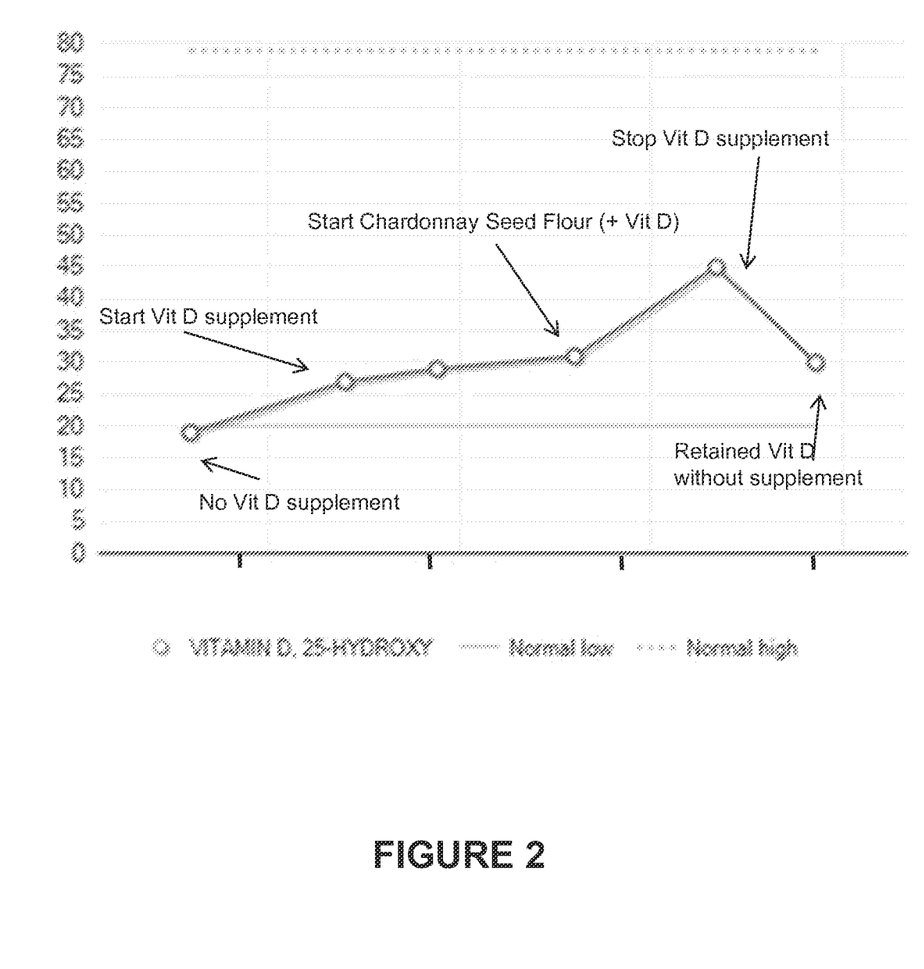
FIG. 2. Illustrates 25-hydroxyvitamin D levels in the blood of a subject. Distance between hashmarks on the x-axis represents one year.

After 90 days of supplementation with Chardonnay seed flour, the subject's vitamin D levels (as measured by blood levels of 25-hydroxvitamin D) were significantly higher than the subject's vitamin D levels prior to supplementation with Chardonnay seed flour (FIG. 2). The subject subsequently stopped taking the vitamin D supplement but continued to supplement his diet with Chardonnay seed flour 7-10% (w/w). Thirty days after stopping vitamin D supplementation, the subject's vitamin D level had returned to the level previously only observed with dietary vitamin D supplementation (FIG. 2).

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the embodiments.

What is claimed is:

1. A method of treating joint pain in a human in need thereof consisting essentially of administering a therapeutically effective amount of a Chardonnay seed flour or a Chardonnay seed extract to the human in need thereof to effectively treat the joint pain, wherein the joint pain is knee joint pain, wrist joint pain, shoulder joint pain, elbow joint pain, ankle joint pain, hip joint pain, or finger joint pain.

2. The method of claim 1, wherein the Chardonnay seed extract is a methanol or ethanol extract.

3. The method of claim 1, wherein the Chardonnay seed flour is Chardonnay pomace meal or Chardonnay pomace flour.

4. The method of claim 1, wherein the pain is knee joint pain.

5. The method of claim 1, wherein the pain is wrist joint pain.

6. The method of claim 1, wherein the pain is shoulder joint pain.

7. The method of claim 1, wherein the pain is elbow joint pain.

8. The method of claim 1, wherein the pain is ankle joint pain.

9. The method of claim 1, wherein the pain is hip joint pain.

10. The method of claim 1, wherein the pain is finger joint pain.

* * * * *